US010004672B2

(12) United States Patent
Kerl et al.

(10) Patent No.: US 10,004,672 B2
(45) Date of Patent: Jun. 26, 2018

(54) OXIDATION DYE INCLUDING A COMBINATION OF CROSS-LINKED, AMINATED SILOXANE POLYMERS AND NON-IONIC SURFACTANTS

(71) Applicant: Henkel AG & Co. KGaA, Duesseldorf (DE)

(72) Inventors: Sylvia Kerl, Hamburg (DE); Susanne Hagenow, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days. days.

(21) Appl. No.: 15/584,985

(22) Filed: May 2, 2017

(65) Prior Publication Data

US 2017/0231880 A1  Aug. 17, 2017

Related U.S. Application Data

(63) Continuation of application No. PCT/EP2015/070548, filed on Sep. 9, 2015.

(30) Foreign Application Priority Data

Nov. 3, 2014  (DE) .......... 10 2014 222 374

(51) Int. Cl.
| | |
|---|---|
| *A61Q 5/10* | (2006.01) |
| *A61K 8/25* | (2006.01) |
| *A61K 8/18* | (2006.01) |
| *A61K 8/30* | (2006.01) |
| *A61K 8/36* | (2006.01) |
| *A61K 8/19* | (2006.01) |

(52) U.S. Cl.
CPC .......... *A61K 8/25* (2013.01); *A61K 8/18* (2013.01); *A61K 8/19* (2013.01); *A61K 8/30* (2013.01); *A61K 8/361* (2013.01); *A61Q 5/10* (2013.01)

(58) Field of Classification Search
CPC .......... A61K 8/28; A61K 8/19; A61Q 5/10
See application file for complete search history.

(56) References Cited

U.S. PATENT DOCUMENTS

| | | | |
|---|---|---|---|
| 2014/0161756 A1 | 6/2014 | Beer et al. | |
| 2014/0165301 A1* | 6/2014 | Schweinsberg | A61K 8/898 8/409 |

FOREIGN PATENT DOCUMENTS

| | | |
|---|---|---|
| DE | 102009027678 A1 | 5/2010 |
| EP | 0023899 A2 * 9/1981 | ............... A51K 7/06 |
| EP | 1921105 A1 | 5/2008 |

OTHER PUBLICATIONS

STIC Search Repot dated Jul. 12, 2017.*
PCT International Search Report (PCT/EP2015/070548) dated Apr. 12, 2015.

* cited by examiner

*Primary Examiner* — Eisa B Elhilo
(74) *Attorney, Agent, or Firm* — James J. Cummings

(57) ABSTRACT

A cosmetic agent for dyeing keratin fibers, in particular human hair, includes a combination of a cross-linked, aminated siloxane polymer, a specific non-ionic surfactant, and at least one oxidation dye intermediate and/or one direct dye, wherein the use of the combination of cross-linked, aminated siloxane polymer and non-ionic surfactant leads to an increase in the color intensity.

9 Claims, No Drawings

OXIDATION DYE INCLUDING A COMBINATION OF CROSS-LINKED, AMINATED SILOXANE POLYMERS AND NON-IONIC SURFACTANTS

FIELD OF THE INVENTION

The present invention generally relates to cosmetic agents for dyeing keratinic fibers.

Furthermore, the present invention relates to a packaging unit (kit of parts), which includes a cosmetic agent of the invention and an oxidizing agent preparation.

Moreover, the present invention relates to a method for dyeing keratinic fibers with use of a cosmetic agent of the invention as well as an oxidizing agent preparation.

In addition, the present invention relates to the use of a cosmetic agent of the invention for increasing the color depth.

Lastly, the present invention relates to the use of a packaging unit of the invention for producing an oxidation dyeing agent for dyeing keratinic fibers with an increased color depth.

BACKGROUND OF THE INVENTION

The changing of the shape and color of hair is an important field in modern cosmetics. As a result, the appearance of the hair can be adapted both to current fashion trends and to the individual wishes of the individual consumer. The fashionable color design of hairstyles or the covering of gray or white hair with trendy or natural color tones typically occurs with color-modifying agents. Apart from a high coloring performance, these agents should have additional properties, such as, for example, the increase in hair volume.

Various coloring systems are known in the prior art for providing color-modifying cosmetic agents, in particular, for the skin or for keratin-containing fibers such as, for example, human hair.

Oxidation dyeing agents are used for permanent, intensive colors with suitable fastness properties. Such dyeing agents customarily include oxidation dye precursors, so-called developer components and coupler components. Under the influence of oxidizing agents or atmospheric oxygen, the developer components form the actual dyes with one another or during coupling with one or more coupler components. The oxidation dyeing agents are characterized by excellent, long-lasting coloring results. For natural-looking colors, customarily a mixture of a relatively large number of oxidation dye precursors must be used; in many cases, direct dyes are used, furthermore, for providing nuances.

Dyeing or tinting agents, which include so-called direct dyes as the coloring component, are customarily used for temporary colors. These are dye molecules that are directly absorbed onto the keratinic fibers and do not require any oxidative process to develop the color. These dyes include, for example, henna which was already known in antiquity for dyeing skin and hair. As a rule, these colors are markedly more sensitive to shampooing than oxidative colors, so that an often undesirable shift in shades or even a visible homogeneous color loss occurs much earlier.

Lastly, a further dyeing method has attracted great interest. In this method, precursors of the natural hair dye melanin are applied to, e.g., hair; these then form bioanalogous dyes in the course of oxidative processes in the hair. 5,6-Dihydroxyindoline, for example, is used as the dye precursor in a method of this kind. Particularly in the case of the repeated use of agents which include 5,6-dihydroxyindoline, it is possible to restore the natural hair color in persons with gray hair. Coloring can occur here with atmospheric oxygen as the sole oxidizing agent, so that other oxidizing agents need not be used. In persons originally having medium-blond to brown hair, 5,6-dihydroxyindoline can be used as the sole dye precursor. For use in persons having an originally red and in particular dark to black hair color, in contrast, satisfactory results can often be achieved only by the concurrent use of further dye components, in particular special oxidation dye precursors.

However, the oxidative dyeing agents known in the prior art do not always lead to the desired high coloring performance, in particular to a high color depth.

Accordingly, it is desirable to provide a cosmetic agent for dyeing keratinic fibers, which avoids or at least reduces the disadvantages of the prior art and which results in an improved color depth. Furthermore, other desirable features and characteristics of the present invention will become apparent from the subsequent detailed description of the invention and the appended claims, taken in conjunction with this background of the invention.

BRIEF SUMMARY OF THE INVENTION

A first subject of the invention, therefore, is a cosmetic agent for changing the color of keratinic fibers, comprising, in a cosmetically acceptable carrier,
a) at least one compound, selected from the group of oxidation dye precursors, direct dyes, and mixtures thereof,
b) at least one crosslinked, aminated siloxane polymer that is obtainable by reacting a copolymer, consisting of 3-(2-aminoethylamino)propylmethylsiloxy units and dimethylsiloxy units, with N-morpholinomethyltriethoxysilane, in a total amount of 0.3 to 1.0% by weight, based on the total weight of the cosmetic agent, and
c) at least one nonionic surfactant of the formula (I)

$$R\text{—}O\text{—}(CH_2\text{—}CH_2\text{—}O)_n\text{—}H \qquad (I),$$

where
R stands for a linear or branched alkyl chain having 12 to 16 carbon atoms, and
n stands for integers from 6 to 15.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was now found surprisingly that the addition of a combination of a crosslinked, aminated siloxane polymer and nonionic surfactants to cosmetic agents for dyeing keratinic fibers, in particular human hair, leads to an increase in the color depth. In comparison with dyeing agents of the prior art, which do not include any combination of a crosslinked, aminated siloxane polymer and nonionic surfactants, therefore a significantly reduced total amount of dyes can be used in the cosmetic agents of the invention to achieve a comparable color depth. Moreover, the use of the aforementioned combination does not lead to negative interactions with the other ingredients of the cosmetic agents of the invention, so that a high storage stability is assured.

The term "keratinic fibers or keratin fibers as well" according to the invention is understood to mean pelts, wool, feathers, and human hair. It is particularly preferred in the context of the present invention if the cosmetic agents are used for dyeing human hair.

Furthermore, the term "crosslinked, aminated siloxane polymers" in the context of the present invention is understood to mean polymers in which the silicon atoms are linked via oxygen atoms, i.e., in which Si—O—Si bonds are present, and which have at least one amine group. The term "crosslinked" or "crosslinking" in the context of the invention is to be understood to mean the linking together of polymer chains of the siloxane polymer by covalent chemical bonding with the formation of a network. Said covalent linking of the polymer chains of the siloxane polymer can occur either by direct covalent bonding or be mediated by a molecular fragment bridging the polymer chains. The molecular fragment bonds to the polymer chains of the siloxane polymer, bridged by the molecular fragment, in each case by covalent chemical bonding.

Moreover, the term "nonionic surfactants" is understood to mean amphiphilic (bifunctional) compounds that consist of at least one hydrophobic and at least one hydrophilic moiety and have no cationizable and/or anionizable groups such as, for example, amine groups, carboxylate groups, sulfate groups, or the like. The nonionic surfactants in the context of the present invention exhibit an oriented absorption at interfaces and an aggregation to form micelles and the formation of i phases.

Moreover, the term "fatty alcohols" in the context of the present invention is understood to mean aliphatic, long-chain, monohydric, primary alcohols, which have unbranched hydrocarbon groups having 6 to 30 carbon atoms. The hydrocarbon groups can be saturated but also mono- or polyunsaturated.

Lastly, the term "fatty acids" in the context of the present invention is understood to mean aliphatic monocarboxylic acids with an unbranched carbon chain, which have hydrocarbon groups having 6 to 30 carbon atoms. The hydrocarbon groups can be either saturated or also mono- or polyunsaturated.

The specification of the total amount in regard to the components of the cosmetic agent in the present case, unless specified otherwise, refers to the total amount of active substance of the particular component. Furthermore, the specification of the total amount in regard to the components of the cosmetic agent, unless specified otherwise, refers to the total weight of the oxidizing agent-free cosmetic agent of the invention.

The agents of the invention include a cosmetic carrier. According to the invention, the cosmetic carrier is preferably aqueous, alcoholic, or aqueous-alcoholic. For example, creams, emulsions, gels, or surfactant-containing foaming solutions such as, for example, shampoos, foam aerosols, or other preparations, suitable for use on hair, are used in the context of the present invention.

An aqueous carrier in the context of the invention includes, based on the total weight of the cosmetic agent, at least 30% by weight, in particular at least 50% by weight of water.

Aqueous-alcoholic carriers in the context of the present invention are to be understood to be water-containing compositions, which include a $C_1$-$C_4$ alcohol in a total amount of 3 to 90% by weight, based on the total weight of the cosmetic agent, in particular ethanol or isopropanol.

The agents of the invention can include in addition other organic solvents such as, for example, methoxybutanol, ethyl diglycol, 1,2-propylene glycol, n-propanol, n-butanol, n-butylene glycol, glycerol, diethylene glycol monoethyl ether, and diethylene glycol mono-n-butyl ether. Preferred in this case are all water-soluble organic solvents, the solvent being included in a total amount of 0.1 to 30% by weight, preferably of 1 to 20% by weight, in particular of 2 to 10% by weight, based on the total weight of the cosmetic agent.

The cosmetic agent of the invention includes as a first essential component a) a compound selected from the group of oxidation dye precursors (ODP), direct dyes (DD), and mixtures thereof.

In one preferred embodiment, the agents of the invention include at least one oxidation dye precursor.

Oxidation dye precursors based on their reaction behavior can be divided into two categories, so-called developer components and coupler components. Developer components can form the actual dye with themselves. They can therefore be present as the only compounds in the cosmetic agent of the invention. In one preferred embodiment, the cosmetic agents of the invention therefore include at least one oxidation dye precursor of the developer type. It can also be provided in the context of the present invention, however, that the cosmetic agents of the invention include at least one oxidation dye precursor of the coupler type. Especially good results are obtained in regard to the dyeing of keratinic fibers, if the cosmetic agents of the invention include at least one oxidation dye precursor of the developer type and at least one oxidation dye precursor of the coupler type.

The developer and coupler components are usually used in the free form. In the case of substances with amino groups, however, it can be preferred to use the salt form thereof, in particular in the form of the hydrochlorides and hydrobromides or sulfates.

Cosmetic agents are preferred according to the invention that include the developer and/or coupler components each in a total amount of 0.001 to 10% by weight, primarily of 0.01 to 8% by weight, preferably of 0.1 to 5% by weight, in particular of 0.5 to 3% by weight, based on the total weight of the cosmetic agent.

In another preferred embodiment, the cosmetic agent of the invention is therefore characterized in that it includes an oxidation dye precursor of the developer and/or coupler type in a total amount of 0.001 to 5.0% by weight, primarily of 0.01 to 4.0% by weight, preferably of 0.1 to 3.0% by weight, in particular of 0.5 to 2.0% by weight, based on the total weight of the cosmetic agent.

Suitable oxidation dye precursors of the developer type are, for example, p-phenylenediamine and the derivatives thereof. Preferred p-phenylenediamines are selected from one or more compounds of the group formed by p-phenylenediamine, p-toluylenediamine, 2-chloro-p-phenylenediamine, 2,3-dimethyl-p-phenylenediamine, 2,6-dimethyl-p-phenylenediamine, N,N-bis(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine, and N-(4-amino-3-methylphenyl)-N-[3-(1H-imidazol-1-yl)propyl]amine, and the physiologically acceptable salts thereof.

It can be preferable, furthermore, according to the invention to use compounds that include at least two aromatic rings substituted with amino and/or hydroxyl groups as the developer component. Preferred bicyclic developer components are selected from N,N'-bis(2-hydroxyethyl)-N,N'-bis (4'-aminophenyl)-1,3-diaminopropan-2-ol, N,N'-bis(4-aminophenyl)-1,4-diazacycloheptane, bis(2-hydroxy-5-aminophenyl)methane, and the physiologically acceptable salts thereof.

It can be preferred, furthermore, according to the invention to use a p-aminophenol derivative or one of the physiologically acceptable salts thereof as a developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and the physiologically acceptable salts thereof.

Further, the developer component can be selected from o-aminophenol and the derivatives thereof, preferably from 2-amino-4-methylphenol, 2-amino-5-methylphenol, 2-amino-4-chlorophenol, and/or the physiologically acceptable salts thereof.

Furthermore, the developer component can be selected from heterocyclic developer components, such as pyrimidine derivatives, pyrazole derivatives, pyrazolopyrimidine derivatives, or the physiologically acceptable salts thereof. Preferred pyrimidine derivatives are 2,4,5,6-tetraaminopyrimidine, 4-hydroxy-2,5,6-triaminopyrimidine, and the physiologically acceptable salts thereof. A preferred pyrazole derivative is 4,5-diamino-1-(2-hydroxyethyl)pyrazole and the physiologically acceptable salts thereof. Pyrazolo [1,5-a]pyrimidines are preferred in particular as pyrazolopyrimidines.

Preferred oxidation dye precursors of the developer type are selected from the group, formed by p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl) methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of said compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, and the physiologically acceptable salts thereof.

According to a further preferred embodiment of the present invention, the cosmetic agent of the invention includes as the oxidation dye precursor, apart from at least one developer component, furthermore, in addition at least one coupler component. M-Phenylenediamine derivatives, naphthols, resorcinol and resorcinol derivatives, pyrazolones, and m-aminophenol derivatives are generally used as coupler components.

Coupler components preferred according to the invention are selected from
a) m-aminophenol and derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)amino-2-methylphenol, and 2,4-dichloro-3-aminophenol,
b) o-aminophenol and derivatives thereof, such as 2-amino-5-ethylphenol,
c) m-diaminobenzene and derivatives thereof such as, for example, 2,4-diaminophenoxyethanol, 1,3-bis(2',4'-diaminophenoxy)propane, 1-methoxy-2-amino-4-(2'-hydroxyethylamino)benzene, 2,6-bis(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}amino)ethanol,
d) o-diaminobenzene and derivatives thereof,
e) di- or trihydroxybenzene derivatives, in particular resorcinol, 2-chlororesorcinol, 4-chlororesorcinol, 2-methylresorcinol, and 1,2,4-trihydroxybenzene,
f) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
g) naphthalene derivatives, such as 1-naphthol and 2-methyl-1-naphthol,
h) morpholine derivatives, such as 6-hydroxybenzomorpholine,
i) quinoxaline derivatives,
j) pyrazole derivatives, such as 1-phenyl-3-methylpyrazol-5-one,
k) indole derivatives, such as 6-hydroxyindole,
l) pyrimidine derivatives, or
m) methylenedioxybenzene derivatives, such as 1-(2'-hydroxyethyl)amino-3,4-methylenedioxybenzene,
and the physiologically acceptable salts thereof.

Coupler components preferred according to the invention are selected from the group, formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethyl)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-2-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically acceptable salts of the aforementioned compounds.

Coupler components particularly preferred according to the invention are resorcinol, 2-methylresorcinol, 5-amino-2-methylphenol, 3-aminophenol, 2-(2,4-diaminophenoxy) ethanol, 1,3-bis(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5- dihydroxynaphthalene, 2,7-dihydroxynaphthalene, and 1-naphthol, and the physiologically acceptable salts thereof.

In one preferred embodiment of the present invention, the cosmetic agents of the invention are characterized in that they include as the oxidation dye precursor at least one developer component, selected from the group comprising p-phenylenediamine, p-toluylenediamine, N,N-bis(2-hydroxyethyl)amino-p-phenylenediamine, 1,3-bis[(2-hydroxyethyl-4'-aminophenyl)amino]propan-2-ol, 1,10-bis(2',5'-diaminophenyl)-1,4,7,10-tetraoxadecane, 4-aminophenol, 4-amino-3-methylphenol, bis(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)pyrazole, physiologically acceptable salts thereof and mixtures thereof, and at least one coupler component, selected from the group comprising resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorophenol, 2,4-diaminophenoxyethanol, 2-amino-4-(2'-hydroxyethyl)aminoanisole sulfate, 1,3-bis(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-one, 2,6-bis[(2'-hydroxyethyl)amino]toluene, 4-hydroxyindole, 6-hydroxyindole, 6-hydroxybenzomorpholine, physiologically acceptable salts thereof, and mixtures thereof.

Particularly preferred in the context of the present invention are cosmetic agents that include as an oxidation dye precursor at least one developer component from the group comprising p-phenylenediamine, in particular p-toluylenediamine, and at least one coupler component from the group comprising resorcinol, resorcinol derivatives, in particular 4-chlororesorcinol, and m-aminophenols, in particular 3-aminophenol, and salts and mixtures thereof.

To obtain a balanced and subtle shade formation, it can also be provided in the context of the present invention that the cosmetic agents of the invention in addition include at least one direct dye. Direct dyes are dyes that are directly absorbed onto the hair and do not require any oxidative process to develop the color. Direct dyes are usually nitrophenylenediamines, nitroaminophenols, azo dyes, anthraquinones, or indophenols.

Direct dyes can be divided into anionic, cationic, and nonionic direct dyes.

Preferred anionic direct dyes are the compounds known under the names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and tetrabromophenol blue. Preferred cationic direct dyes are cationic triphenylmethane dyes, such as Basic Blue 7, Basic Blue 26, Basic Violet 2, and Basic Violet 14, and aromatic systems, which are substituted with a quaternary nitrogen group, such as Basic Yellow 57, Basic Red 76, Basic Blue 99, Basic Brown 16, and Basic Brown 17, and HC Blue 16, as well as Basic Yellow 87, Basic Orange 31, and Basic Red 51. Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, naturally occurring dyes as well can be used as direct dyes, as are found, for example, in henna red, henna neutral, henna black, chamomile blossoms, sandalwood, black tea, walnut, buckthorn bark, sage, logwood, madder root, catechu, and alkanna root.

Preferably the cosmetic agent of the invention includes the direct dyes in a total amount of 0.001 to 10% by weight, primarily of 0.01 to 8% by weight, preferably of 0.1 to 5% by weight, in particular of 0.5 to 3% by weight, based on the total weight of the cosmetic agent.

The cosmetic agents of the invention include as the second essential component b) at least one crosslinked, aminated siloxane polymer. The addition of said siloxane polymer in combination with the nonionic surfactant leads to an increase in the color depth and therefore allows the dye amount to be reduced. Furthermore, the crosslinked, aminated siloxane polymers are stable relative to the oxidizing agents used for dyeing and do not lead to negative interactions with the other ingredients of the cosmetic agent of the invention, so that a high storage stability is assured.

In the context of the invention, crosslinked, aminated siloxane polymers are used with preference that are obtainable by reacting specific amounts of the copolymer, consisting of 3-(2-aminoethylamino)propylmethylsiloxy units and dimethylsiloxy units, with specific amounts of N-morpholinomethyltriethoxysilane. Particularly preferred embodiments of the present invention are therefore characterized in that the at least one crosslinked, aminated siloxane polymer b) is obtainable by reacting a copolymer, consisting of 3-(2-aminoethylamino)propylmethylsiloxy units and dimethylsiloxy units, with N-morpholinomethyltriethoxysilane in a weight ratio of 100:1 to 10:1, primarily of 80:1 to 20:1, preferably of 70:1 to 30:1, in particular of 55:1 to 45:1.

According to a preferred embodiment of the present invention, the at least one crosslinked, aminated siloxane polymer b) has an average molecular weight $M_w$ of 2000 to 1,000,000 g/mol, in particular of 5000 to 200,000 g/mol. Special crosslinked, aminated siloxane polymers, which have the aforementioned average molecular weight $M_w$, result in an especially good improvement of the color depth. The average molecular weight $M_w$ can be determined, for example, by gel permeation chromatography (GPC) (Liu X. M. et al.; "*Comparative studies of poly(dimethylsiloxanes) using automated GPC-MALDI-TOF MS and on-line GPC-ESI-TOF MS*"; J. Am. Soc. Mass. Spectrom., 2003, 14, pages 195 to 202).

Especially good results in the context of the present invention are obtained, if the at least one crosslinked, aminated siloxane polymer b) is present as an emulsion, wherein the emulsion has an average particle size $D_{50}$ of 3 to 500 nm, primarily of 10 to 400 nm, preferably of 50 to 300 nm, in particular of 100 to 300 nm. The use of emulsions of this kind, in which the crosslinked, aminated siloxane polymer has specific average particle sizes, according to the invention leads to an especially great increase in the color depth. The average particle size $D_{50}$ can be determined, for example, by dynamic light scattering (DLS) (Bergna H. E. et. al.; "Colloidal Silica—Fundamentals and Application"; Surfactant Science Series, CRC Press, 2006, 131, pages 65 to 80).

The cosmetic agents of the invention include the at least one crosslinked, aminated siloxane polymer b) in a total amount of 0.4 to 0.9% by weight, preferably of 0.5 to 0.8% by weight, in particular of 0.6 to 0.8% by weight, based on the total weight of the cosmetic agent. The use of the aforementioned total amount of the special crosslinked, aminated siloxane polymer leads to an increased color depth and, to achieve a comparable color depth compared with prior art oxidation dyeing agents, therefore, allows a significant reduction in the total amount of employed dyes. If, in contrast, amounts of more than 1.0% by weight of the crosslinked, aminated siloxane polymer are employed, thus a reduction in the color depth is observed instead of the increase in the color depth. Therefore, only the use of the crosslinked, aminated siloxane polymer in the aforementioned narrow amount ranges leads an increase of the invention in the color depth.

The cosmetic agent of the invention includes at least one nonionic surfactant of the formula (I) as the third essential ingredient c).

It is preferred in the context of the present invention, if in the formula (I) R stands for a linear or branched alkyl chain having 12 to 14 carbon atoms, in particular having 13 carbon atoms, and n for integers from 7 to 12, primarily from 8 to 11, preferably from 9 or 10, in particular 10. The combination of special nonionic surfactants with crosslinked, aminated siloxane polymers in oxidation dyeing agents leads to an increase in the color depth. The compound known under the INCI name Trideceth-10 (polyoxyethylene (10) tridecyl ether) is used particularly preferably as the nonionic surfactant.

The nonionic surfactant is preferably used in specific amounts in the cosmetic agents of the invention. Preferred embodiments of the present invention are therefore characterized in that the cosmetic agent includes the at least one nonionic surfactant c) of the formula (I) in a total amount of 0.0005 to 10% by weight, primarily of 0.001 to 8.0% by weight, preferably of 0.005 to 5.0% by weight, in particular of 0.01 to 1.0% by weight. The use of the aforementioned amounts of nonionic surfactants leads to a sufficient emulsification of the particulate, crosslinked, aminated siloxane polymer and in this way assures a homogeneous distribution of the crosslinked, aminated siloxane polymer in the cosmetic agents of the invention. A homogeneous dyeing is made possible in this way and the uniform increase in the color depth in all areas of the keratinic fibers is assured.

It emerged that an addition of special dimethylcyclosiloxanes can stabilize the at least one crosslinked, aminated siloxane polymer in the cosmetic agents of the invention, so that the increase in the color depth is enhanced. Cosmetic agents preferred according to the invention therefore include in addition at least one dimethylcyclosiloxane in a total amount of 0.001 to 2.0% by weight, preferably of 0.05 to 1.5% by weight, in particular of 0.01 to 1.0% by weight, based on the total weight of the cosmetic agent, the at least one dimethylcyclosiloxane having the formula (II)

where
z stands for integers from 2 to 8, primarily from 2 to 6, preferably from 2 to 4, in particular for the integer 4.

The cosmetic agents of the invention can include other active substances and additives. It is therefore preferred in the context of the present invention, if the cosmetic agent includes in addition at least one further compound, selected from the group comprising (i) thickeners; (ii) linear or branched, saturated or unsaturated alcohols having 8 to 20 carbon atoms; (iii) surfactants, in particular amphoteric surfactants; (iv) alkalizing agents; (v) oils; as well as (vi) mixtures thereof.

Preferably, the cosmetic agents of the invention are formulated as flowable preparations. In this case, the cosmetic agents should be formulated so that, on the one hand, they can be applied and distributed well at the application site but, on the other, are sufficiently viscous, so that they remain at the site of action during the contact time and do not run.

It has proven advantageous according to the invention, therefore, if the cosmetic agents of the invention include at least one thickener from the group comprising (i) anionic, synthetic polymers; (ii) cationic, synthetic polymers; (iii) naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin, and dextrins, as well as cellulose derivatives such as, for example, methylcellulose, carboxyalkyl celluloses, and hydroxyalkyl celluloses; (iv) nonionic, synthetic polymers, such as polyvinyl alcohol or polyvinylpyrrolidinone; (v) inorganic thickeners, in particular phyllosilicates such as, for example, bentonite, particularly smectites, such as montmorillonite or hectorite; as well as (vi) mixtures thereof, in a total amount of 0.0005 to 5.0% by weight, primarily of 0.001 to 3.0% by weight, preferably of 0.005 to 1.0% by weight, in particular of 0.008 to 0.01% by weight, based on the total weight of the cosmetic agent.

It has emerged as advantageous in this regard, if at least one naturally occurring thickener, in particular xanthan gum and salts thereof, is included as a thickener in a total amount of 0.0005 to 5.0% by weight, primarily of 0.001 to 1.0% by weight, preferably of 0.005 to 0.5% by weight, in particular of 0.01 to 0.2% by weight, based on the total weight of the cosmetic agent.

Furthermore, the cosmetic agents of the invention can include at least one linear or branched, saturated or unsaturated alcohol having 8 to 20 carbon atoms. It can be preferred in this regard, if the linear or branched, saturated or unsaturated alcohol having 8 to 20 carbon atoms is selected from the group comprising myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), primarily 2-octyldodecanol and/or cetearyl alcohol, and is included in a total amount of 1.0 to 35% by weight, primarily of 5.0 to 30% by weight, preferably of 10 to 25% by weight, in particular of 12 to 20% by weight, based on the total weight of the cosmetic agent.

Preferably the cosmetic agents of the invention can include, furthermore, at least one partial ester of a polyol having 2 to 6 carbon atoms and linear saturated carboxylic acids having 12 to 30, in particular 14 to 22 carbon atoms, wherein the partial esters can be hydroxylated, in a total amount of 0.5 to 10% by weight, in particular of 3.0 to 8.0% by weight, based on the total weight of the cosmetic agent. Such partial esters are in particular the mono- and diesters of glycerol or the monoesters of propylene glycol or the mono- and diesters of ethylene glycol or the mono-, di-, tri-, and tetraesters of pentaerythritol in each case with linear saturated $C_{12}$-$C_{30}$ carboxylic acids, which may be hydroxylated, in particular those with palmitic and stearic acid, the sorbitan mono-, di-, or triesters of linear saturated $C_{12}$-$C_{30}$ carboxylic acids, which may be hydroxylated, in particular those of myristic acid, palmitic acid, stearic acid, or of mixtures of these fatty acids and the methyl glucose mono- and diesters of linear saturated $C_{12}$-$C_{30}$ carboxylic acids, which may be hydroxylated.

It can therefore be provided in this regard that the cosmetic agents of the invention include at least one polyol partial ester, selected from glycerol monostearate, glycerol monopalmitate, glycerol distearate, glycerol dipalmitate, ethylene glycol monostearate, ethylene glycol monopalmitate, ethylene glycol distearate, ethylene glycol dipalmitate, and mixtures thereof, in particular mixtures of glycerol monostearate, glycerol monopalmitate, glycerol distearate, and glycerol dipalmitate in a total amount of 0.5 to 10% by weight, in particular of 3.0 to 8.0% by weight, based on the total weight of the cosmetic agent.

The use of the aforementioned alcohols, partial esters, and poly partial esters in the cosmetic agents of the invention can be particularly preferred when the cosmetic agents of the invention are present in the form of an oil-in-water emulsion.

It can be provided according to the invention, furthermore, that the cosmetic agents according to the invention include at least one surfactant, which is different from the nonionic surfactant c) of the formula (I).

According to one preferred embodiment of the present invention, the cosmetic agents of the invention include at least one amphoteric surfactant in a total amount of 0.1 to 5.0% by weight, in particular of 0.2 to 2.0% by weight, based on the total weight of the cosmetic agent. Such surface-active compounds that have at least one quaternary ammonium group and at least one —$COO^{(-)}$ or —$SO3^{(-)}$ group can be called amphoteric or zwitterionic surfactants.

The compounds listed below are particularly preferred as amphoteric surfactants in the context of the present invention:
  alkyl betaines having 8 to 20 carbon atoms in the alkyl group,
  amidopropyl betaines having 8 to 20 carbon atoms in the acyl group,
  sulfobetaines having 8 to 20 carbon atoms in the acyl group, and
  amphoacetates or amphodiacetates having 8 to 20 carbon atoms in the acyl group.

In a particularly preferred embodiment, the cosmetic agents of the invention include as a surfactant at least one amphoteric surfactant, selected from amidopropyl betaines having 9 to 13 carbon atoms in the acyl group, in a total amount of 0.1 to 5.0% by weight, in particular of 0.2 to 2.0% by weight, based on the total weight of the cosmetic agent.

It can be provided, furthermore, that the cosmetic agents of the invention include at least one ethoxylated nonionic surfactant, which is different from the nonionic surfactant c) of the formula (I), in a total amount of 0.5 to 6.0% by weight, in particular of 1.0 to 4.0% by weight, based on the total weight of the cosmetic agent. In this case, it has emerged as especially advantageous, if the ethoxylated nonionic surfactant has an HLB value above 10, preferably above 13. It is necessary to this end that the nonionic surfactant has a sufficiently high ethoxylation degree. In this regard, the cosmetic agent of the invention therefore includes as the ethoxylated nonionic surfactant at least one ethoxylated surfactant with at least 12 ethylene oxide units. Apart from the suitably ethoxylated fatty alcohols, in particular lauryl alcohol, myristyl alcohol, cetyl alcohol, stearyl alcohol, arachyl alcohol, and behenyl alcohol, in particular the adducts of 20 to 60 mol of ethylene oxide to castor oil and hydrogenated castor oil are especially suitable according to the invention. The at least one ethoxylated nonionic surfactant is preferably selected from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of these substances, selected particularly preferably from Ceteth-20, Steareth-20, Ceteareth-20, Ceteth-30, Steareth-30, and Ceteareth-30.

Cosmetic agents in the context of the present invention normally have a basic pH value, in particular between pH 8.0 and pH 12. These pH values are necessary to assure an opening of the outer cuticle layer (cuticle) and to enable penetration of the oxidation dye precursors and/or the oxidizing agent into the hair.

The aforementioned pH value can be established preferably with the use of an alkalizing agent. In the context of the present invention, the alkalizing agent is selected from the group of (i) inorganic alkalizing agents; (ii) organic alkalizing agents; and (iii) mixtures thereof, and in a total amount of 1.5 to 9.5% by weight, primarily of 2.5 to 8.5% by weight, preferably of 3.0 to 8.0% by weight, in particular of 3.5 to 7.5% by weight, based on the total weight of the cosmetic agent.

Preferred inorganic alkalizing agents are selected from the group formed by ammonia or ammonium hydroxide, therefore aqueous solutions of ammonia, sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof. Ammonia or ammonium hydroxide is a particularly preferred alkalizing agent. Ammonia is particularly preferred in a total amount of 0.1 to 20% by weight, preferably of 0.5 to 10% by weight, in particular of 1.0 to 7.0% by weight, based on the total weight of the cosmetic agent.

Preferred organic alkalizing agents are selected from at least one alkanolamine. Alkanolamines preferred according to the invention are selected from alkanolamines of primary, secondary, or tertiary amines with a $C_2$-$C_6$ alkyl parent structure, bearing at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1, 3-diol, 2-amino-2-ethyl-1,3-propanediol, N,N-dimethylethanolamine, triethanolamine, diethanolamine, and triisopropanolamine. Alkanolamines very particularly preferred according to the invention are selected from the group comprising 2-aminoethan-1-ol (monoethanolamine), 2-amino-2-methylpropan-1-ol, 2-amino-2-methylpropane-1,3-diol, and triethanolamine. Particularly preferred cosmetic agents of the invention include a mixture of monoethanolamine and 2-amino-2-methylpropan-1-ol. Preferably the at least one alkanolamine is included in a total amount of 0.05 to 15% by weight, preferably of 0.5 to 10% by weight, and in particular of 3.5 to 7.5% by weight, based on the total weight of the cosmetic agent.

Other organic alkalizing agents preferred according to the invention are selected from basic amino acids, particularly preferably selected from the group formed by L-arginine, D-arginine, D/L-arginine, L-lysine, D-lysine, D/L-lysine, and mixtures thereof. Basic amino acids particularly preferred according to the invention are selected from L-arginine, D-arginine, and D/L-arginine. Preferred cosmetic agents of the invention include at least one alkalizing agent, different from alkanolamines and ammonia, in a total amount of 0.05 to 5.0% by weight, in particular of 0.5 to 3.0% by weight, based on the total weight of the cosmetic agent.

In a particularly preferred embodiment, the cosmetic agents of the invention include as alkalizing agents a mixture of at least two alkanolamines different from one another, in particular of monoethanolamine and 2-amino-2-methylpropan-1-ol, in a total amount of 0.05 to 15% by weight, preferably of 0.5 to 10% by weight, in particular of 3.5 to 7.5% by weight, based on the total weight of the cosmetic agent.

Preferably, the pH value of the cosmetic agents of the invention, measured at 22° C., is 8 to 13, primarily 9.5 to 12, preferably 10 to 11.5, in particular 10.5 to 11.

In the context of the present invention, it can be preferred, furthermore, if the cosmetic agents of the invention include at least one oil, selected from the group comprising sunflower oil, corn oil, soy oil, pumpkin seed oil, grape seed oil, sesame oil, hazelnut oil, apricot kernel oil, macadamia nut oil, arara oil, castor oil, avocado oil, and mixtures thereof, in a total amount of 0.1 to 10% by weight, preferably of 0.2 to 5.0% by weight, and in particular of 0.5 to 2.0% by weight, based on the total weight of the cosmetic agent.

Particularly preferably, the cosmetic agents of the invention include grape seed oil in a total amount of 0.1 to 10% by weight, preferably of 0.2 to 5.0% by weight, in particular of 0.5 to 2.0% by weight, based on the total weight of the cosmetic agent.

According to a particularly preferred embodiment of the present invention, the cosmetic agents of the invention present as an oil-in-water emulsion include, based on the total weight of the cosmetic agents, cetearyl alcohol in a total amount of 2.0 to 20% by weight, in particular of 5.0 to 18% by weight, further mixtures of glycerol monostereate, glycerol monopalmitate, glycerol distearate, and glycerol dipalmitate in a total amount of 0.5 to 10% by weight, preferably 3.0 to 8.0% by weight, further at least one amphoteric surfactant, selected from amidopropyl betaines having 9 to 13 carbon atoms in the acyl group, in a total amount of 0.1 to 5.0% by weight, in particular of 0.2 to 2.0% by weight, further a mixture of at least two alkanolamines different from one another, in particular of monoethanolamine and 2-amino-2-methylpropan-1-ol, in a total amount of 0.05 to 15% by weight, preferably of 0.5 to 10% by weight, in particular of 3.5 to 7.5% by weight, further grape seed oil in a total amount of 0.1 to 10% by weight, preferably of 0.2 to 5.0% by weight, in particular of 0.5 to 2.0% by weight.

Oxidative dye compositions can also be prepared immediately before use from two or more separately packaged compositions. This lends itself in particular to separating incompatible ingredients in order to prevent a premature reaction. Separation into multi-component systems is preferred particularly when incompatibilities of the ingredients are a possibility or a risk. The oxidative dye composition in these cases is prepared by the consumer immediately before use by mixing the components. In the context of the present invention, this procedure is particularly preferred in the case of oxidative dyes, in which the cosmetic agent of the invention is present initially separated from an oxidizing agent preparation which includes at least one oxidizing agent.

A further subject of the present invention therefore is a packaging unit (kit of parts), comprising, produced separately from one another,
a) at least one container (C1), containing a cosmetic agent of the invention, and
b) at least one container (C2), containing an oxidizing agent preparation, which includes at least one oxidizing agent and at least one acid in a cosmetically acceptable carrier.

The term "container" in the context of the present invention is understood to mean an enclosure, which is present in the form of an optionally reclosable bottle, tube, box, a small packet, sachet, or similar enclosures. No limits are imposed on the wrapping material according to the invention. Preferably, however, these are enclosures made of glass or plastic.

The oxidizing agents in the context of the present invention are different from atmospheric oxygen. Hydrogen peroxide and the solid adducts thereof to organic and inorganic compounds can be used as oxidizing agents. Solid adducts suitable according to the invention are in particular the adducts to urea, melamine, polyvinylpyrrolidinone, and sodium borate. Hydrogen peroxide and/or one of its solid adducts to organic or inorganic compounds are particularly preferred as oxidizing agents. Preferably according to the invention, the oxidizing agent is therefore selected from the group of persulfates, chlorites, hydrogen peroxide, and adducts of hydrogen peroxide to urea, melamine, and sodium borate, in particular hydrogen peroxide.

A particularly preferred embodiment of the present invention is therefore characterized in that the oxidizing agent in the oxidizing agent preparation (M2) is hydrogen peroxide and is included in a total amount of 0.5 to 7.0% by weight, preferably of 1.0 to 7.0% by weight, and in particular of 3.0 to 7.0% by weight, based on the total weight of the oxidizing agent preparation (M2). The calculation of the total amount in this case refers to 100% $H_2O_2$.

The oxidizing agent preparations, furthermore, can include water in a total amount of 40 to 98% by weight, in particular of 65 to 85% by weight, based on the total weight of the oxidizing agent preparation (M2).

According to a preferred embodiment of the present invention, the oxidizing agent preparations include further at least one linear saturated alkanol having 12 to 30 carbon atoms, in particular having 16 to 22 carbon atoms, in a total amount of 0.1 to 10% by weight, primarily of 0.5 to 5.0% by weight, in particular of 1.0 to 4.0% by weight, based on the total weight of the oxidizing agent preparation (M2). Preferred in particular are cetyl alcohol, stearyl alcohol, arachidyl alcohol, behenyl alcohol, and lanolin alcohol or mixtures of said alcohols, as they are obtainable in the large-scale hydrogenation of plant and animal fatty acids, and mixtures of said alkanols. The cetearyl alcohol mixture is particularly preferred.

In a further preferred embodiment of the present invention, the oxidizing agent preparations include at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of said substances, selected particularly preferably from Ceteth-20, Steareth-20, Ceteareth-20, Ceteth-30, Steareth-30, and Ceteareth-30, in a total amount of 0.1 to 10% by weight, preferably of 0.5 to 5.0% by weight, in particular of 1 to 4.0% by weight, based on the total weight of the oxidizing agent preparation (M2).

In the context of the present invention, it can also be provided in addition that the oxidizing agent preparations include at least one ester from a carboxylic acid having 10 to 20 carbon atoms and a linear or branched alcohol having 1 to 5 carbon atoms, in particular isopropyl myristate, in a total amount of 3.0 to 25% by weight, primarily of 5.0 to 20% by weight, in particular of 8.0 to 15% by weight, based on the total weight of the oxidizing agent preparation (M2).

According to a particularly preferred embodiment of the present invention, the oxidizing agent preparations (M2) include, based on the total weight of the oxidizing agent preparations (M2), at least one linear saturated alkanol having 12 to 30 carbon atoms in a total amount of 0.1 to 10% by weight, preferably of 0.5 to 5.0% by weight, in particular of 1.0 to 4.0% by weight, further at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of said substances, selected particularly preferably from Ceteth-20, Steareth-20, Ceteareth-20, Ceteth-30, Steareth-30, and Ceteareth-30, in a total amount of 0.1 to 10% by weight, preferably of 0.5 to 5.0% by weight, in particular of 1.0 to 4.0% by weight, and at least one ester from a carboxylic acid having 10 to 20 carbon atoms and a linear or branched alcohol having 1 to 5 carbon atoms, preferably isopropyl myristate, in a total amount of 3.0 to 25% by weight, preferably of 5.0 to 20% by weight, in particular of 8.0 to 15% by weight.

The oxidizing agent preparations of the invention include, furthermore, at least one acid. Preferred acids are selected from dipicolinic acid, edible acids such as, for example, citric acid, acetic acid, malic acid, lactic acid, and tartaric acid, dilute mineral acids such as hydrochloric acid, phosphoric acid, pyrophosphoric acid, and sulfuric acid, and mixtures thereof.

The oxidizing agent preparations preferably have a pH value, measured at 22° C., in the range of 2 to 5, in particular of 3 to 4.

To prepare oxidative dye compositions from the packaging unit of the invention (kit of parts), the cosmetic agent of the invention (M1) in container C1 is mixed with the oxidizing agent preparation (M2) in container C2 or vice versa.

It can be especially advantageous according to the invention, further, if the packaging unit includes at least one further hair treatment agent in an additional container, in particular a conditioning agent preparation. Said conditioning agent preparation advantageously includes at least one conditioning agent, selected from the group of cationic polymers, silicone derivatives, and oils. Moreover, the packaging unit can comprise application aids, such as combs, brushes, dye brushes, or small brushes, personal protective clothing, in particular disposable gloves, and optionally instructions for use. A dye brush is understood to be a broad brush which has a point at the handle end which permits and simplifies the separation of fiber bundles or strands from the total amount of fibers.

The statements made about the cosmetic agents of the invention apply mutatis mutandis to the cosmetic agent of the invention (M1) in container (C1) and the oxidizing agent preparation (M2) in container (C2).

A further subject of the present invention is a method for dyeing keratinic fibers, wherein the method comprises the following process steps:

a) providing a cosmetic agent of the invention (M1),
b) providing an oxidizing agent preparation (M2), which includes in a cosmetically acceptable carrier at least one oxidizing agent and at least one acid,
c) mixing the cosmetic agent (M1) with the oxidizing agent preparation (M2),
d) applying the mixture obtained in step c) to the keratinic fibers and leaving said mixture on the keratinic fibers for a time period of 10 to 60 minutes, preferably of 20 to 45 minutes, at room temperature and/or at at least 30° C.,
e) rinsing the keratinic fibers with water and/or a cleansing composition for 1 to 5 minutes, and
f) optionally applying an aftertreatment agent to the keratinic fibers and rinsing it off after a time period of 1 to 10 minutes.

The method of the invention for dyeing keratinic fibers with the use of a combination of a special crosslinked, aminated siloxane polymer and a nonionic surfactant results in an increased color depth of the dyed keratinic fibers. As a result, to achieve a comparable color depth the total amount of dyes can be significantly reduced compared with prior art dyeing agents.

Room temperature in the context of the present invention is understood to be the ambient temperature. The effect of the coloring and/or lightening preparation can be intensified by an external heat supply, for example, by means of a heating hood. The preferred contact time of the coloring and/or lightening preparation on the keratinic fiber is 10 to 60 minutes, preferably 20 to 45 minutes. After the contact time ends, the remaining dyeing agent is washed out of the keratinic fibers with the aid of a cleansing preparation, which preferably includes at least one cationic and/or anionic and/or nonionic surfactant, and/or water. Optionally, the process is repeated with a further agent. After the washing out, the keratinic fibers are optionally rinsed with an aftertreatment agent, for example, a conditioning agent, and dried with a towel or a hot air dryer. The application of the dye preparation usually occurs by hand by the user. Preferably, in this case, personal protective clothing is worn, in particular suitable protective gloves, for example, made of plastic or latex for one-time use (disposable gloves), and optionally an apron. It is also possible, however, to apply the dyeing agents to the keratinic fibers with an application aid.

The statements made about the cosmetic agents of the invention and the packaging unit of the invention apply mutatis mutandis to the cosmetic agent of the invention (M1), the oxidizing agent preparation (M2), and further preferred embodiments of the method.

Moreover, a further subject of the present invention is the use of a cosmetic agent of the invention for increasing the color depth. The use of the combination of a special cross-linked, aminated siloxane polymer with a nonionic surfactant leads to an increased color depth and therefore allows the significant reduction of the total amount of dyes to achieve a comparable color depth compared with prior art dyeing agents.

The statements made about the cosmetic agents of the invention, the packaging unit of the invention, and the method of the invention apply mutatis mutandis to other preferred embodiments of the use of the invention.

Lastly, a further subject of the present invention is the use of a packaging unit of the invention (kit of parts) for producing a cosmetic agent for changing the color of keratinic fibers with an increased color depth.

The statements made about the cosmetic agents of the invention, the packaging unit of the invention, and the method of the invention apply mutatis mutandis to other preferred embodiments of the use of the invention.

The present invention is outlined in particular by following points:

A cosmetic agent for changing the color of keratinic fibers, which includes, in a cosmetically acceptable carrier,
a) at least one compound, selected from the group of oxidation dye precursors, direct dyes, and mixtures thereof,
b) at least one crosslinked, aminated siloxane polymer that is obtainable by reacting a copolymer, consisting of 3-(2-aminoethylamino)propylmethylsiloxy units and dimethylsiloxy units, with N-morpholinomethyltriethoxysilane, in a total amount of 0.3 to 1.0% by weight, based on the total weight of the cosmetic agent, and
c) at least one nonionic surfactant of the formula (I)

$$R-O-(CH_2-CH_2-O)_n-H \qquad (I),$$

where
R stands for a linear or branched alkyl chain having 12 to 16 carbon atoms, and
n stands for integers from 6 to 15.

The cosmetic agent according to point 1, characterized in that the cosmetic agent includes the oxidation dye precursor, in particular the developer and/or coupler component(s), in a total amount of 0.001 to 5.0% by weight, primarily of 0.01 to 4.0% by weight, preferably of 0.1 to 3.0% by weight, in particular of 0.5 to 2.0% by weight, based on the total weight of the cosmetic agent.

The cosmetic agent according to one of points 1 or 2, characterized in that the at least one crosslinked, aminated siloxane polymer b) is obtainable by reacting a copolymer, consisting of 3-(2-aminoethylamino)propylmethylsiloxy units and dimethylsiloxy units, with N-morpholinomethyltriethoxysilane in a weight ratio of 100:1 to 10:1, primarily of 80:1 to 20:1, preferably of 70:1 to 30:1, in particular of 55:1 to 45:1.

The cosmetic agent according to one of the preceding points, characterized in that the at least one crosslinked, aminated siloxane polymer b) has an average molecular weight $M_w$ of 2000 to 1,000,000 g/mol, in particular of 5000 to 200,000 g/mol.

The cosmetic agent according to one of the preceding points, characterized in that the at least one aminated siloxane polymer b) is present as an emulsion, wherein the emulsion has an average particle size $D_{50}$ of 3 to 500 nm, primarily of 10 to 400 nm, preferably of 50 to 300 nm, in particular of 100 to 300 nm.

The cosmetic agent according to one of the preceding points, characterized in that the cosmetic agent includes the at least one crosslinked, aminated siloxane polymer b) in a total amount of 0.4 to 0.9% by weight, preferably of 0.5 to 0.8% by weight, in particular of 0.6 to 0.8% by weight.

The cosmetic agent according to one of the preceding points, characterized in that in the formula (I) R stands for a linear or branched alkyl chain having 12 to 14 carbon atoms, in particular having 13 carbon atoms, and n for integers from 7 to 12, primarily from 8 to 11, preferably from 9 or 10, in particular 10.

The cosmetic agent according to one of the preceding points, characterized in that the cosmetic agent includes the at least one nonionic surfactant c) of the formula (I) in a total amount of 0.0005 to 10% by weight, primarily of 0.001 to 8.0% by weight, preferably of 0.005 to 5.0% by weight, in particular of 0.01 to 1.0% by weight.

The cosmetic agent according to one of the preceding points, characterized in that the cosmetic agent includes in addition at least one dimethylcyclosiloxane in a total amount of 0.001 to 2.0% by weight, preferably of 0.05 to 1.5% by weight, in particular of 0.01 to 1.0% by weight, based on the total weight of the cosmetic agent, the at least one dimethylcyclosiloxane having the formula (II)

$$\left[ \begin{array}{c} Me \\ | \\ Si-O \\ | \\ Me \end{array} \right]_z, \qquad (II)$$

where
z stands for integers from 2 to 8, primarily from 2 to 6, preferably from 2 to 4, in particular for the integer 4.

The cosmetic agent according to one of the preceding points, characterized in that the cosmetic agent includes in addition at least one further compound, selected from the group of thickeners, linear or branched, saturated or unsaturated alcohols having 8 to 20 carbon atoms, alkalizing agents, and mixtures thereof.

The cosmetic agent according to point 10, characterized in that at least one naturally occurring thickener, in particular xanthan gum and salts thereof, is included as a thickener in a total amount of 0.0005 to 5.0% by weight, primarily of 0.001 to 1.0% by weight, preferably of 0.005 to 0.5% by weight, in particular of 0.01 to 0.2% by weight, based on the total weight of the cosmetic agent.

A packaging unit (kit of parts), comprising, produced separately from one another,
a) at least one container (C1), containing a cosmetic agent (M1) according to one of points 1 to 11, and
b) at least one container (C2), containing an oxidizing agent preparation (M2), which includes at least one oxidizing agent and at least one acid in a cosmetically acceptable carrier.

A method for dyeing keratinic fibers, wherein the method comprises the following process steps:
a) providing a cosmetic agent (M1) according to one of points 1 to 11,
b) providing an oxidizing agent preparation (M2), which includes in a cosmetically acceptable carrier at least one oxidizing agent and at least one acid, c) mixing the cosmetic agent (M1) with the oxidizing agent preparation (M2), d) applying the mixture obtained in step c) to the keratinic fibers and leaving said mixture on the keratinic fibers for a time period of 10 to 60 minutes, preferably of 20 to 45 minutes, at room temperature and/or at at least 30° C., e) rinsing the keratinic fibers with water and/or a cleansing composition for 1 to 5 minutes, and f) optionally applying an aftertreatment agent to the keratinic fibers and rinsing it off after a time period of 1 to 10 minutes.

Use of a cosmetic agent according to one of points 1 to 11 for increasing the color depth.

Use of a packaging unit (kit of parts) according to point 12 for producing a cosmetic agent for changing the color of keratinic fibers with an increased color depth.

The following examples are intended to explain preferred embodiments of the invention, but without restricting them.

Examples

1. Formulations

Compositions of the employed cosmetic agents (oil-in-water emulsions, all amounts given in % by weight). The nonionic surfactant used in the following formulations is preferably a nonionic surfactant of the formula (I), where R stands for a linear alkyl chain having 13 carbon atoms and n for the integer 10.

| Raw material | V1 | V2 | E1* |
|---|---|---|---|
| Xanthan gum | 0.1 | 0.1 | 0.1 |
| 2-Octyldodecanol | 2.3 | 2.3 | 2.3 |
| Lanette N[a)] | 14 | 14 | 14 |
| Cetearyl alcohol | 3.9 | 3.9 | 3.9 |
| Cutina GMS-SE[b)] | 6.0 | 6.0 | 6.0 |
| Glycerol 99.5% | 2.0 | 2.0 | 2.0 |
| Cocamidopropyl betaine, 40% | 2.0 | 2.0 | 2.0 |
| Monoethanolamine | 4.3 | 4.3 | 4.3 |
| 2-Amino-2-methylpropanol | 0.1 | 0.1 | 0.1 |
| Sodium sulfite, anhydrous | 0.2 | 0.2 | 0.2 |
| Caramel syrup, 75% | 0.1 | 0.1 | 0.1 |
| Grape seed oil | 1.0 | 1.0 | 1.0 |
| p-Toluylenediamine sulfate | 0.9 | 0.9 | 0.9 |
| Resorcinol | 0.3 | 0.3 | 0.3 |
| 3-Aminophenol | 0.1 | 0.1 | 0.1 |
| 4-Chlororesorcinol | 0.2 | 0.2 | 0.2 |
| Crosslinked, aminated silicone polymer** | — | 1.4 | 0.7 |
| Nonionic surfactant of the formula (I) | — | 0.1 | 0.05 |
| Water, demineralized | To 100.00 | To 100.00 | To 100.00 |

*according to the invention
**Active substance
[a)]INCI name: Cetearyl alcohol, Sodium cetearyl sulfate (BASF)
[b)]INCI name: Glyceryl stearate (BASF)

The fat base was melted together at 80° C. and dispersed with a portion of the water amount. The remaining formulation components were then incorporated in sequence while stirring. The mixture was then made up with water to 100% by weight and the formulation was stirred until cold. Formulations V1 and V2 are comparison formulations that are not of the invention, without aminated silicone polymer/nonionic surfactant or with a too high amount of crosslinked, aminated siloxane polymer. Formulation E1 is an example of the invention.

Oxidizing Agent Preparation O1 (all Amounts in % by Weight)

| Raw material | O1 |
|---|---|
| Disodium pyrophosphate | 0.10 |
| Dipicolinic acid | 0.10 |
| Potassium hydroxide 50% | 0.30 |
| 1-Hydroxyethane-1,1-diphosphonic acid 60% | 0.40 |
| Emulgade F[c)] | 4.0 |
| Cetearyl alcohol | 0.5 |
| Ceteareth-20 | 0.5 |
| Beeswax | 0.3 |
| Isopropyl myristate | 10 |
| Hydrogen peroxide 50% | 11 |
| Water, demineralized | To 100 |

[c)]INCI name: Cetearyl alcohol, PEG-40 Castor oil, Sodium cetearyl sulfate (BASF)

2. Increasing the Color Depth

To prepare the oxidative dyeing agents for determining the color depth, the cosmetic agents V1, V2, and E2 were mixed in each case in a 1:1 weight ratio with the above oxidizing agent preparation O01.

The oxidative dyeing agents prepared in this way were each applied in a defined amount (4 g of the oxidative dyeing agent per 1 g of yak hair) to yak hair strands (12 strands each per oxidative dyeing agent) and remained on the hair strands for a contact time of 30 minutes at 32° C. Next, the remaining agents were each rinsed out of the hair strands for 2 minutes with lukewarm water; the strands were first dried with a towel and then blown dry.

All strands were measured with a colorimeter from the company Datacolor, Spectraflash 450 type. The dL value used for evaluating the color depth results from the L color values, measured using the particular strands, as follows:

$dL = L_i - L_0$ $L_0$ in this case are the averages of the color values, determined from 12 measurements, of yak hair strands treated with oxidative dyeing agent V1, whereas $L_i$ represent the averages of the color values after the oxidative dyeing of hair strands with oxidative dyeing agents V2 and E1.

The lower the dL value, the greater the color depth. The dL values for the colors with use of cosmetic agents V2 and E1 are presented in the following table. The colors with cosmetic agent E2 of the invention, which includes the special crosslinked, aminated siloxane polymer in a total amount of 0.7% by weight and a special nonionic surfactant, have an increased color depth compared with dyeing agent V1 without the crosslinked, aminated siloxane polymer/nonionic surfactant. In contrast, colors with cosmetic agent V2 that is not of the invention, which includes the crosslinked, aminated siloxane polymer in a total amount of more than 1% by weight, namely, 1.4% by weight, exhibit a reduced color depth compared with dyeing agents V1 without the crosslinked, aminated siloxane polymer/nonionic surfactant.

| Oxidative dyeing agents | dL |
|---|---|
| V2 + O1 (1:1) | −0.84 |
| E1 + O1 (1:1) | +2.76 |

Apart from the dL value, furthermore, the relative color strength can be used to determine an increase or decrease in the color depth. The relative color strength is determined as follows based on the lightness value L relative color strength[%] = $(L_0/L_i) * 100$ $L_0$ in this case are the averages of the color values, determined from 12 measurements, of yak hair strands treated with oxidative dyeing agent V1, whereas $L_i$ represent the averages of the color values after the oxidative dyeing of hair strands with oxidative dyeing agents V2 and E1.

A value of 100% for the relative color strength in this case means that the colors achieved with dyeing agents V2 and E1 have an identical lightness as the color achieved with dyeing agent V1. The color depth of dyeing agents V2 and E1 in this case is identical to the color depth of dyeing agent V1. Values above 100% signify an increased color depth compared with comparison composition V1, whereas values below 100% stand for a reduced color depth in comparison with V1. The relative color strengths of dyeing agents V2 and E1 are summarized in the following table. Dyeing agent E1 of the invention has a relative color strength of more than 100%, i.e., a higher color depth than comparison composition V1 without the crosslinked, aminated siloxane polymer/nonionic surfactant. In contrast, dyeing agent V2 that is not of the invention, with a total weight of crosslinked, aminated siloxane polymer of more than 1% by weight has a relative color strength of less than 100% and therefore a reduced color depth compared with comparison composition V1 without the crosslinked, aminated siloxane polymer/nonionic surfactant.

| Oxidative dyeing agents | Relative color strength [%] |
|---|---|
| V2 + 01 (1:1) | 104 |
| E1 + 01 (1:1) | 81.3 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic agent for changing the color of keratinic fibers, including, in a cosmetically acceptable carrier,
   a) at least one compound, selected from the group consisting of oxidation dye precursors, direct dyes, and mixtures thereof,
   b) at least one crosslinked, aminated siloxane polymer that is obtainable by reacting a copolymer, wherein the copolymer is produced by reacting monomers consisting of 3-(2-aminoethylamino)propylmethylsiloxy units and dimethylsiloxy units, and wherein said copolymer is crosslinked with N-morpholinomethyltriethoxysilane, and wherein said crosslinked, aminated siloxane polymer is present in the cosmetic agent in a total amount of 0.3 to 1.0% by weight, based on the total weight of the cosmetic agent, and
   c) at least one nonionic surfactant of the formula (I)

$$R\text{—}O\text{—}(CH_2\text{—}CH_2\text{—}O)_n\text{—}H \quad (I),$$

wherein R stands for a linear or branched alkyl chain having 12 to 16 carbon atoms, and n stands for integers from 6 to 15.

2. The cosmetic agent according to claim 1, wherein the at least one crosslinked, aminated siloxane polymer b) is present as an emulsion, and wherein the emulsion has an average particle size $D_{50}$ of 3 to 500 nm.

3. The cosmetic agent according to claim 1, wherein the cosmetic agent includes the at least one crosslinked, aminated siloxane polymer b) in a total amount of 0.4 to 0.9% by weight.

4. The cosmetic agent according to claim 1, wherein in the formula (I) R is a linear or branched alkyl chain having 12 to 14 carbon atoms, and n is an integer from 7 to 12.

5. The cosmetic agent according to claim 1, wherein the cosmetic agent includes the at least one nonionic surfactant c) of the formula (I) in a total amount of 0.0005 to 10% by weight.

6. The cosmetic agent according to claim 1, further including at least one dimethylcyclosiloxane in a total amount of 0.001 to 2.0% by weight based on the total weight of the cosmetic agent, the at least one dimethylcyclosiloxane having the formula (II)

wherein z is an integer from 2 to 8.

7. A packaging unit (kit of parts), comprising, produced separately from one another,
   a) at least one container (C1), containing a cosmetic agent (M1), wherein said cosmetic agent (M1) comprises;
      (i) at least one compound, selected from the group consisting of oxidation dye precursors, direct dyes, and mixtures thereof;
      (ii) at least one crosslinked, aminated siloxane polymer that is obtainable by reacting a copolymer, wherein the copolymer is produced by reacting monomers consisting of 3-(2-aminoethylamino)propylmethylsiloxy units and dimethylsiloxy units, and wherein said copolymer is crosslinked with N-morpholinomethyltriethoxysilane, and wherein said crosslinked, aminated siloxane polymer is present in the cosmetic agent in a total amount of 0.3 to 1.0% by weight, based on the total weight of the cosmetic agent and
      (iii) at least one nonionic surfactant of the formula (I)

$$R\text{—}O\text{—}(CH_2\text{—}CH_2\text{—}O)_n\text{—}H \quad (I),$$

wherein R stands for a linear or branched alkyl chain having 12 to 16 carbon atoms, and n stands for integers from 6 to 15; and
   b) at least one container (C2), containing an oxidizing agent preparation (M2), which includes at least one oxidizing agent and at least one acid in a cosmetically acceptable carrier.

8. A method for dyeing keratinic fibers, wherein the method comprises:
   a) providing a cosmetic agent (M1), wherein said cosmetic agent (M1) comprises;
      (i) at least one compound, selected from the group consisting of oxidation dye precursors, direct dyes, and mixtures thereof;

(ii) at least one crosslinked, aminated siloxane polymer that is obtainable by reacting a copolymer, wherein the copolymer is produced by reacting monomers consisting of 3-(2-aminoethylamino)propylmethylsiloxy units and dimethylsiloxy units, and wherein said copolymer is crosslinked with N-morpholinomethyltriethoxysilane, and wherein said crosslinked, aminated siloxane polymer is present in the cosmetic agent in a total amount of 0.3 to 1.0% by weight, based on the total weight of the cosmetic agent and (iii) at least one nonionic surfactant of the formula (I)

$$R\text{---}O\text{---}(CH_2\text{---}CH_2\text{---}O)_n\text{---}H \quad (I),$$

wherein R stands for a linear or branched alkyl chain having 12 to 16 carbon atoms, and n stands for integers from 6 to 15; and b) providing an oxidizing agent preparation (M2), including in a cosmetically acceptable carrier at least one oxidizing agent and at least one acid, c) mixing the cosmetic agent (M1) with the oxidizing agent preparation (M2), d) applying the mixture obtained in step c) to the keratinic fibers and leaving said mixture on the keratinic fibers for a time period of 10 to 60 minutes at least at room temperature, e) rinsing the keratinic fibers with water and/or a cleansing composition for 1 to 5 minutes, and f) optionally applying an aftertreatment agent to the keratinic fibers and rinsing it off after a time period of 1 to 10 minutes.

9. The cosmetic agent according to claim 1 wherein the crosslinked, aminated siloxane polymer comprises polymer chains linked together by covalent chemical bonds to form a network.

* * * * *